US011787870B2

(12) United States Patent
Yoon et al.

(10) Patent No.: US 11,787,870 B2
(45) Date of Patent: Oct. 17, 2023

(54) PHARMACEUTICAL COMPOSITION FOR PREVENTING OR TREATING CANCER COMPRISING LRIT2 INHIBITOR AS ACTIVE INGREDIENT

(71) Applicant: GENOME AND COMPANY, Seongnam-si (KR)

(72) Inventors: Kyoung Wan Yoon, Seongnam-si (KR); Youn Kyung Houh, Seongnam-si (KR); Bu-Nam Jeon, Seongnam-si (KR); Jinyoung Sohn, Seongnam-si (KR); Yun Yeon Kim, Seongnam-si (KR); Suro Lee, Seongnam-si (KR); Joo-Yeon Chung, Seongnam-si (KR); Areum Jeong, Seongnam-si (KR)

(73) Assignee: GENOME AND COMPANY, Seongnam-si (KR)

( * ) Notice: Subject to any disclaimer, the term of this patent is extended or adjusted under 35 U.S.C. 154(b) by 338 days.

(21) Appl. No.: 17/041,220

(22) PCT Filed: May 15, 2019

(86) PCT No.: PCT/KR2019/005853
§ 371 (c)(1),
(2) Date: Sep. 24, 2020

(87) PCT Pub. No.: WO2019/221516
PCT Pub. Date: Nov. 21, 2019

(65) Prior Publication Data
US 2021/0009710 A1   Jan. 14, 2021

(30) Foreign Application Priority Data

May 16, 2018  (KR) .................. 10-2018-0055909

(51) Int. Cl.
*C07K 16/28* (2006.01)
*A61P 35/00* (2006.01)
*C12N 15/113* (2010.01)

(52) U.S. Cl.
CPC .......... *C07K 16/2896* (2013.01); *A61P 35/00* (2018.01); *C12N 15/1138* (2013.01); *C07K 2317/55* (2013.01)

(58) Field of Classification Search
CPC ............ C07K 16/2896; C07K 2317/55; C07K 2317/76; C07K 14/705; C07K 16/28; C07K 2319/30; A61P 35/00; A61P 31/00; C12N 15/1138; C12N 2310/14; A61K 2039/505; A61K 38/00
See application file for complete search history.

(56) References Cited

U.S. PATENT DOCUMENTS

| 2015/0050647 A1 | 2/2015 | Luo et al. |
| 2015/0064236 A1 | 3/2015 | Bancel et al. |
| 2017/0095531 A1 | 4/2017 | Schereiber et al. |
| 2017/0151339 A1* | 6/2017 | White ............. A61P 35/00 |

FOREIGN PATENT DOCUMENTS

| WO | WO-2008085797 A2 * | 7/2008 | ......... A61K 31/7088 |
| WO | 2017/120344 A1 | 7/2017 | |
| WO | 2017/211947 A1 | 12/2017 | |

OTHER PUBLICATIONS

Gassling V. et al, Disease-Associated miRNA-mRNA Networks in Oral Lichen Planus, PLoS ONE 8(5):e63015, May 27, 2013 (Year: 2013).*
Al Qaraghuli M. et al, Antibody-protein binding and conformational changes: identifying allosteric signaling pathways to engineer a better effector response, Scientific Reports, 10:13696, 2020 (Year: 2020).*
Seok H. et al, Evaluation and control of miRNA-like off-target repression for RNA interference, Cellular and Molecular Life Sciences, 75, 797-814, Sep. 2017 (Year: 2017).*
Chiu M. et al, Antibody Structure and Function: The Basis for Engineering Therapeutics, Antibodies, 8(4), 55, 2019 (Year: 2019).*
Samuel K. Houston et al., "Regional and Temporal Differences in Gene Expression of LHBETATAG Retinoblastoma Tumors", Investigative Ophthalmology & Visual Science, Jul. 2011, pp. 5359-5368. vol. 52, No. 8.
Akiko Ueno et al., "Lrit1, a Retinal Transmembrane Protein, Regulates Selective Synapse Formation in Cone Photoreceptor Cells and Visual Acuity", Cell Reports, Mar. 27, 2018, pp. 3548-3561, vol. 22.
Krzysztof M. Zak et al., "Structure of the Complex of Human Programmed Death 1, PD-1, and Its Ligand PD-L1", HHS Public Access, Structure, Dec. 1, 2015, pp. 1-18, 23(12).
International Search Report for PCT/KR2019/005853, dated Aug. 20, 2019.
Bylicki et al., "Targeting the PD-1/PD-L1 Immune Checkpoint in EFGR-Mutated or ALK-Translocated non-Small-Cell Lung Cancer", Targ Oncol, 2017, vol. 12, pp. 563-569 (7 pages total).

* cited by examiner

*Primary Examiner* — Daniel E Kolker
*Assistant Examiner* — Brittney E Donoghue
(74) *Attorney, Agent, or Firm* — Sughrue Mion, PLLC

(57) ABSTRACT

The present invention relates to a pharmaceutical composition for preventing or treating cancer, comprising an LRIT2 inhibitor as an active ingredient. The LRIT2 inhibitor according to the present invention can increase the activity of immune cells, and thus can be used as an immune enhancer. Also, the LRIT2 inhibitor according to the present invention can effectively prevent or treat cancer by enhancing the immunity of an individual.

10 Claims, 16 Drawing Sheets
Specification includes a Sequence Listing.

[Fig. 1]
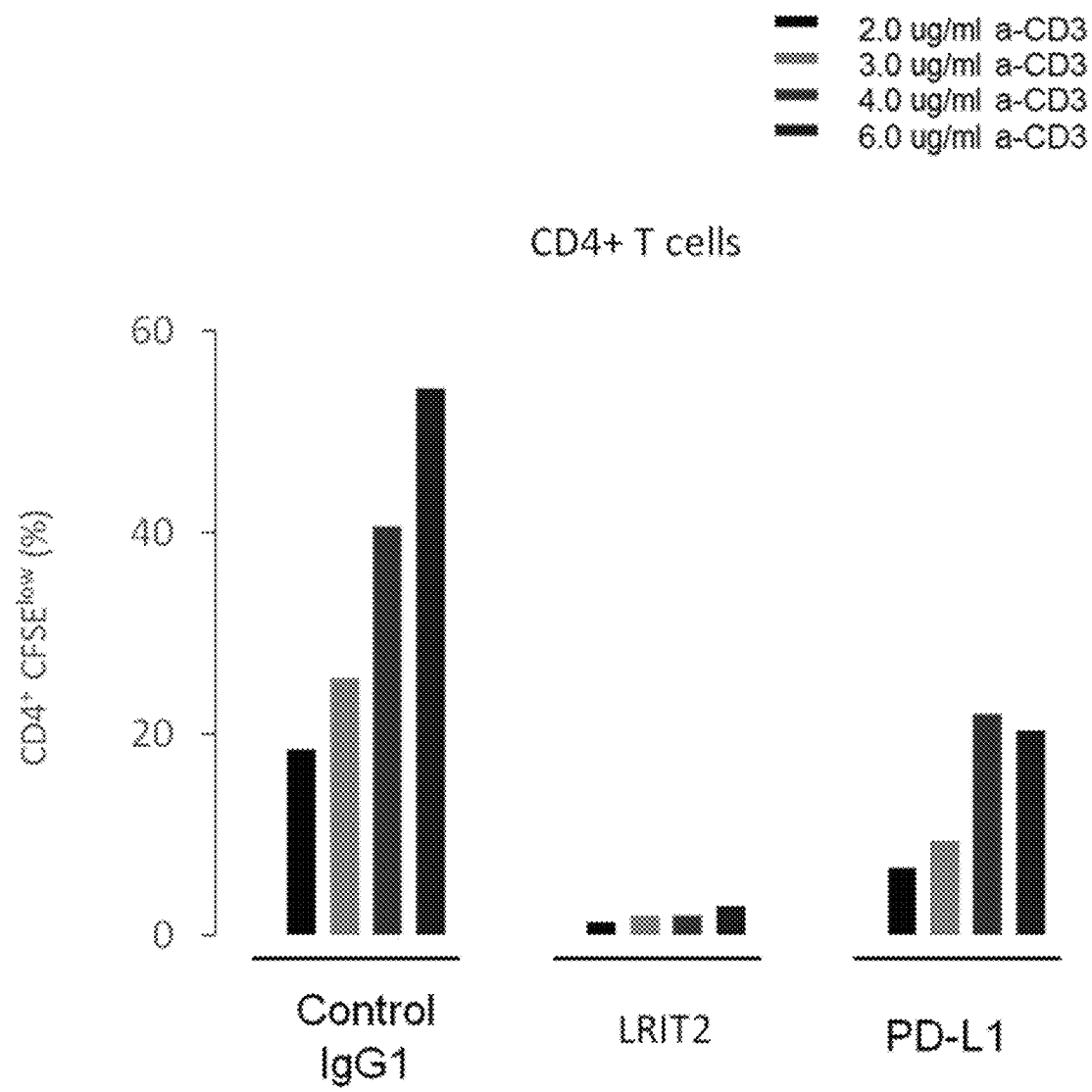

[Fig. 2]
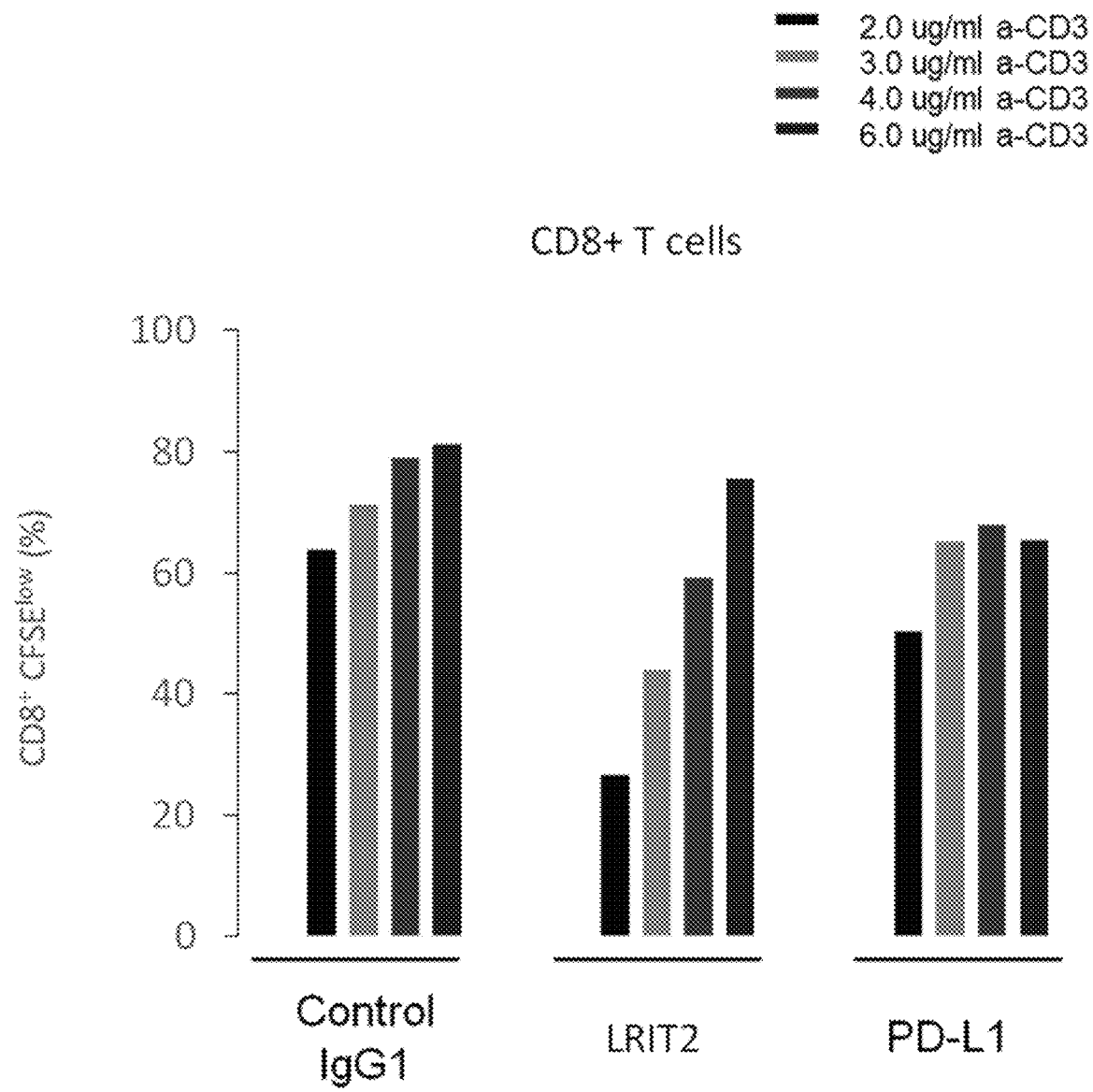

[Fig. 3a]
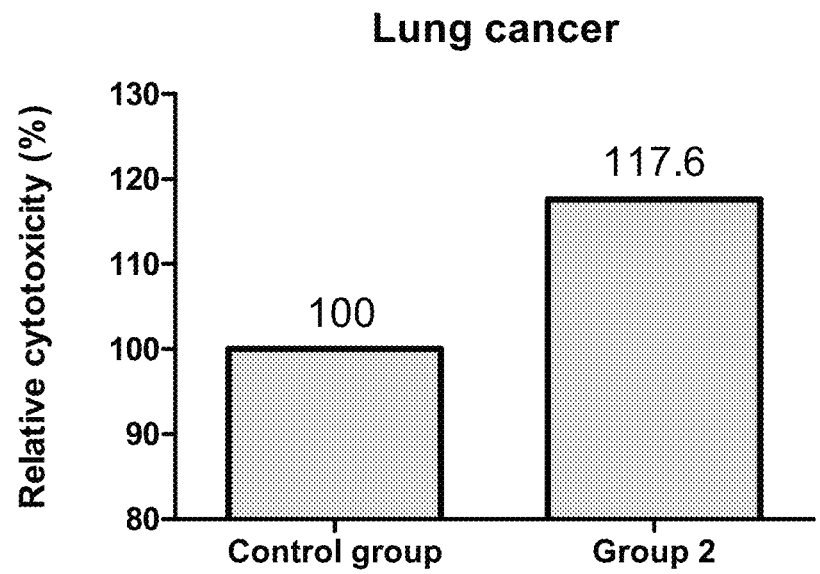
[Fig. 3b]
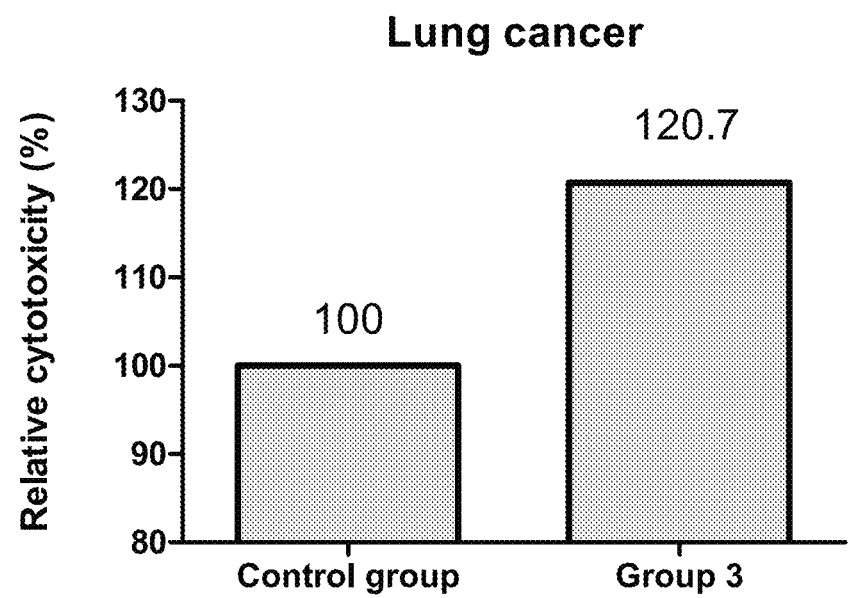

[Fig. 3c]
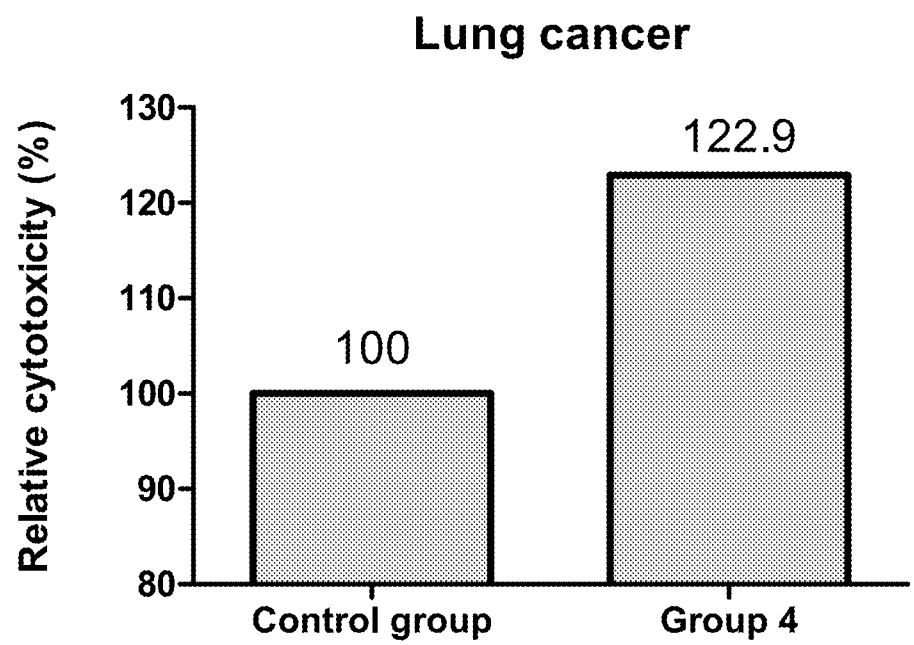
[Fig. 3d]
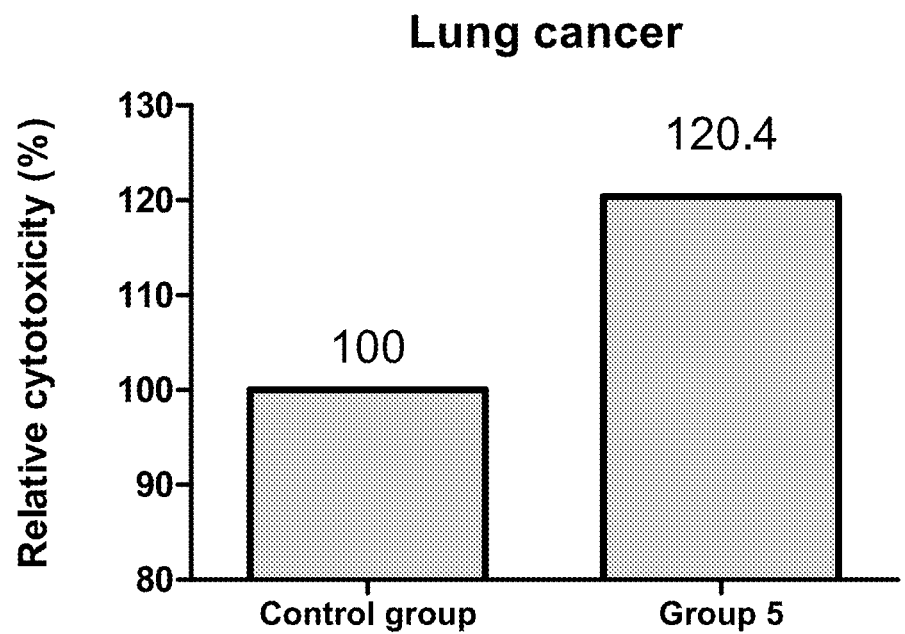

[Fig. 4a]
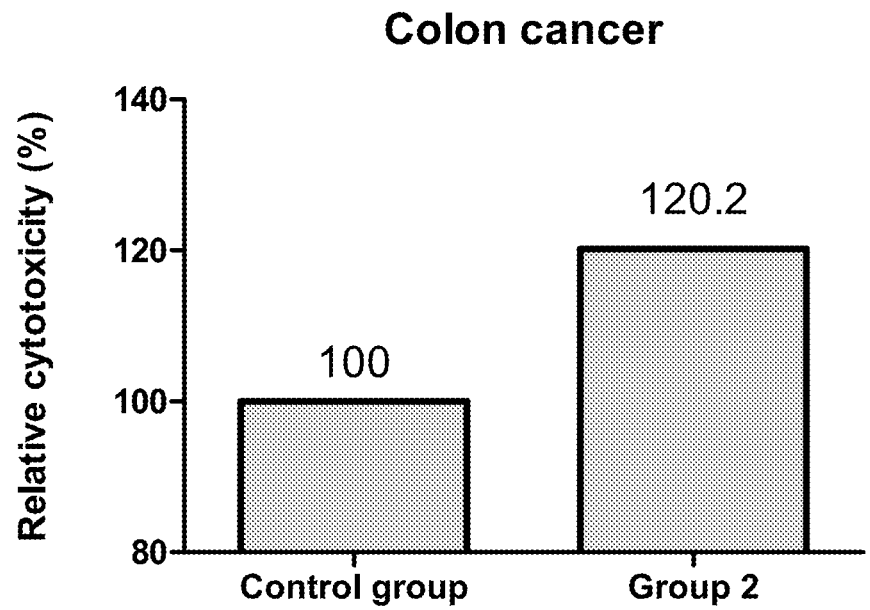
[Fig. 4b]
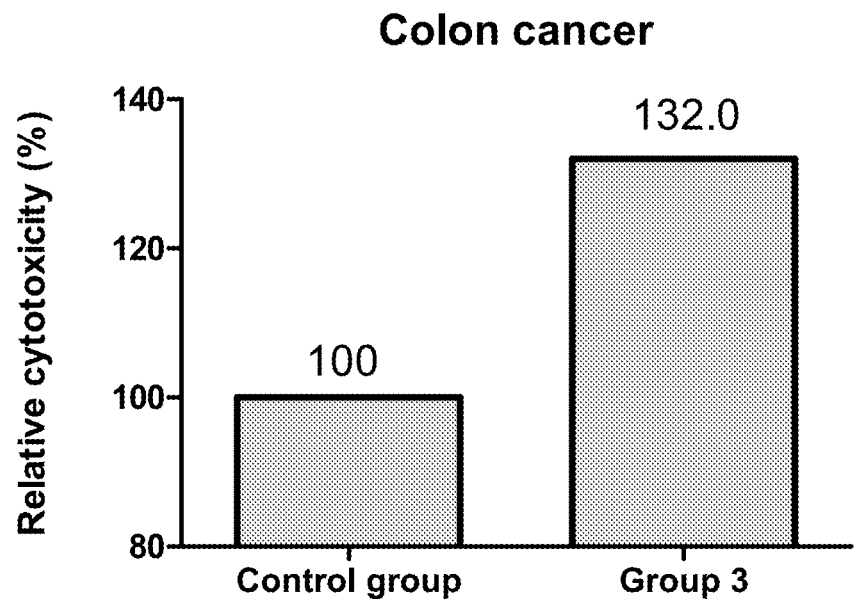

[Fig. 4c]
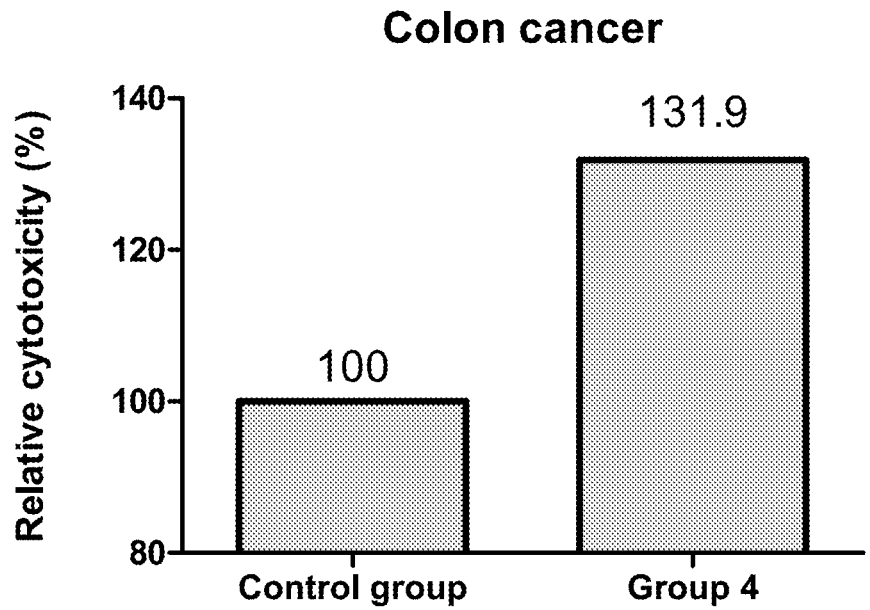
[Fig. 4d]
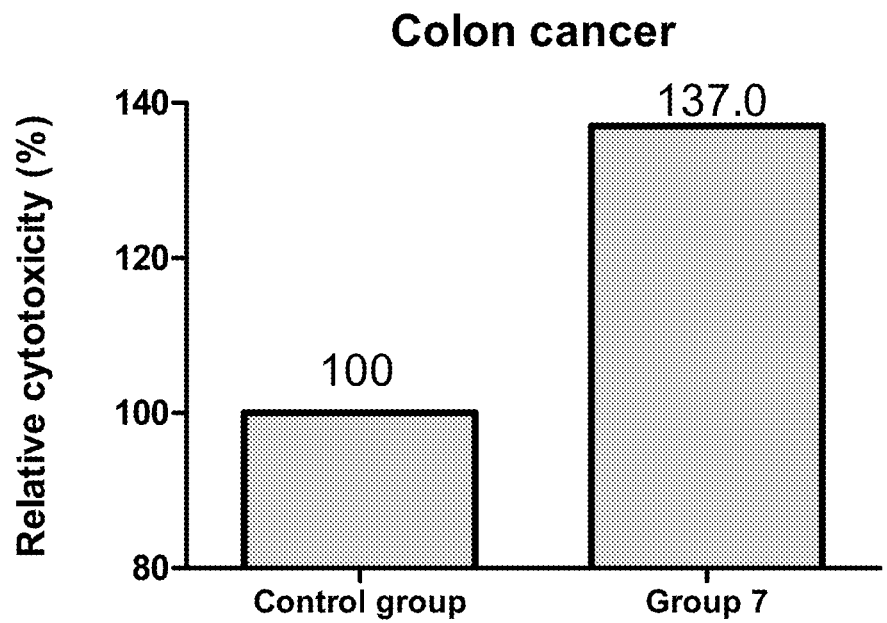

[Fig. 5a]
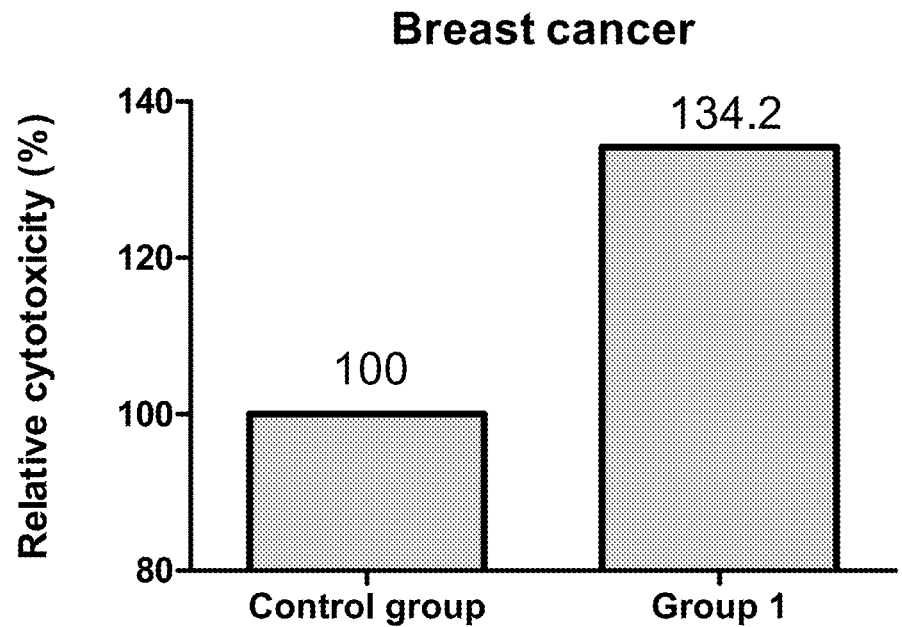
[Fig. 5b]
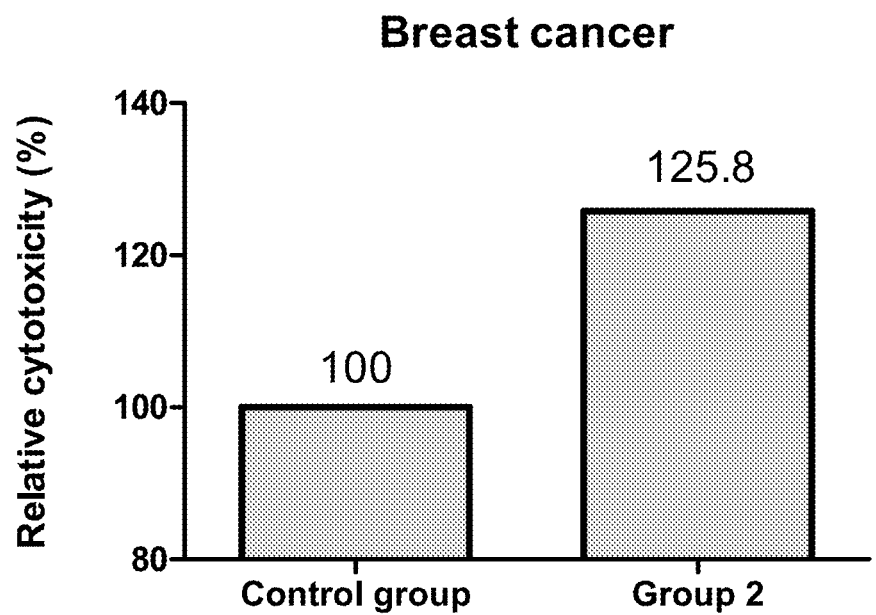

[Fig. 5c]
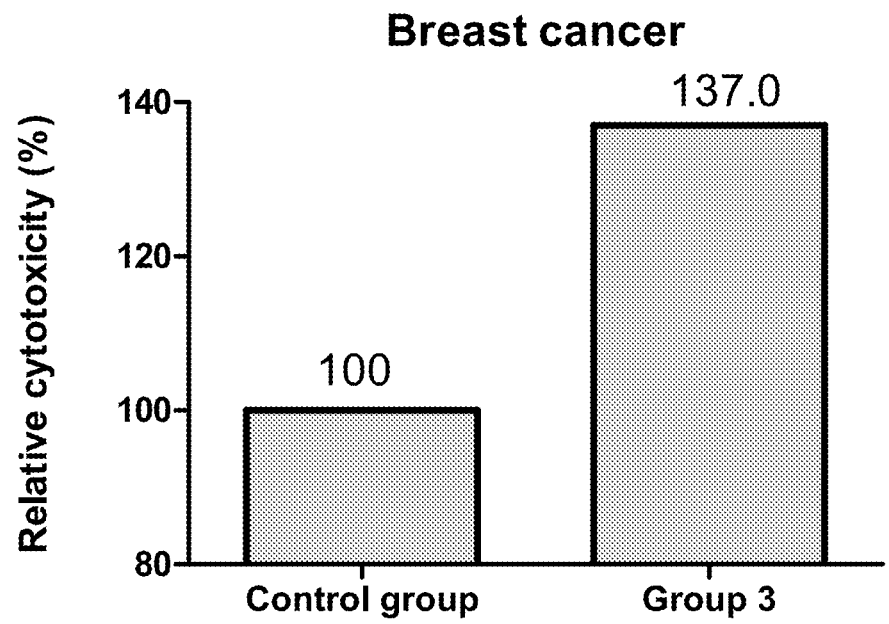
[Fig. 5d]
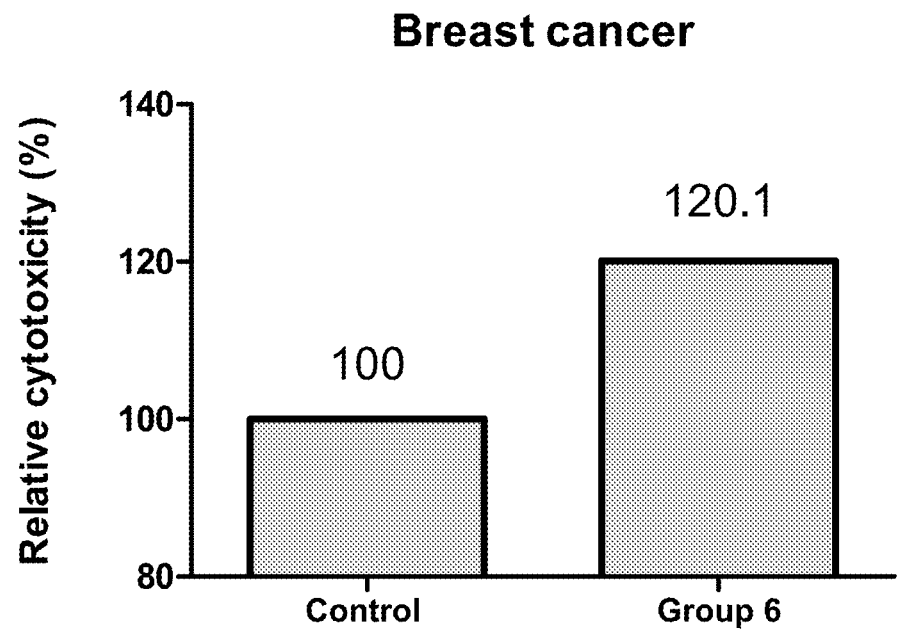

[Fig. 6a]
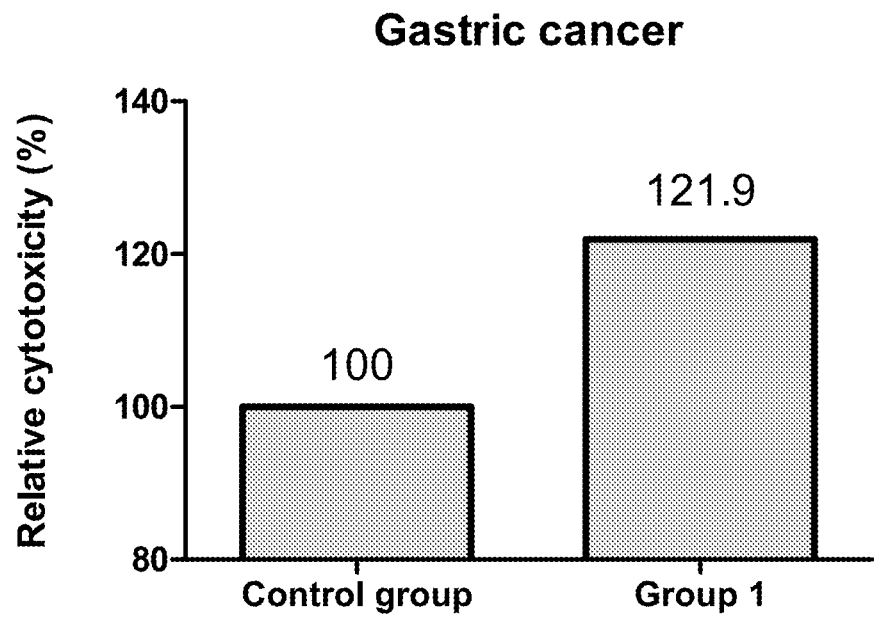
[Fig. 6b]
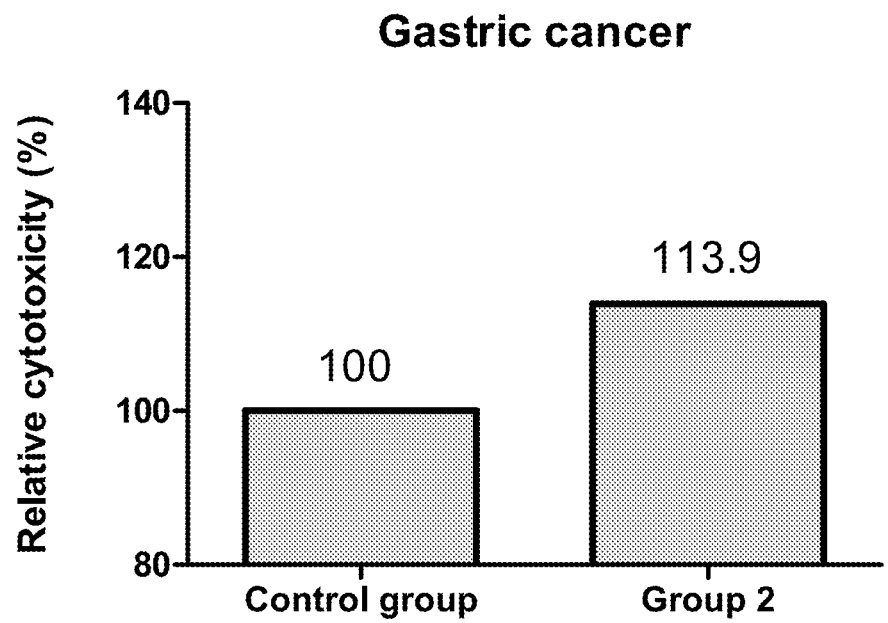

[Fig. 6c]
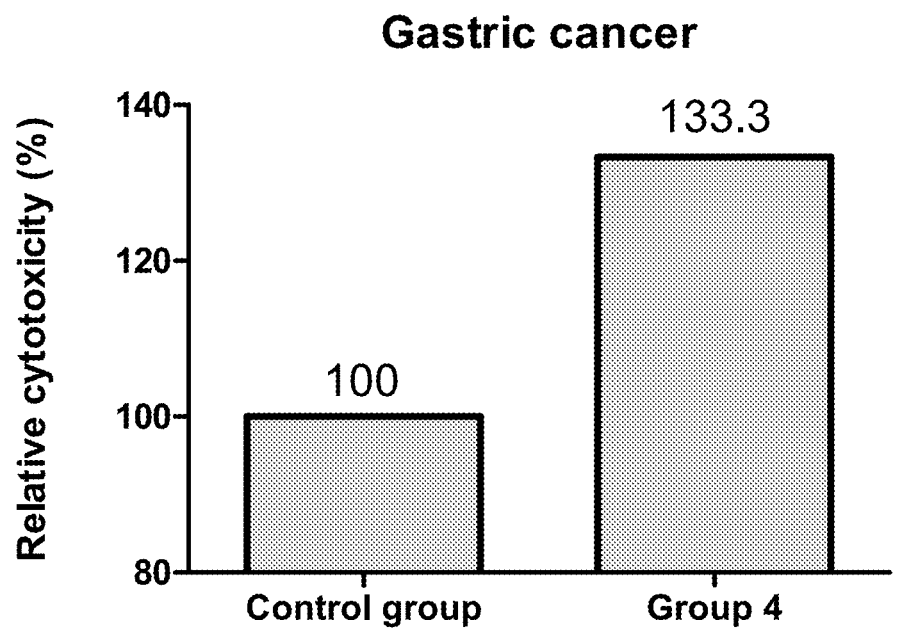
[Fig. 6d]
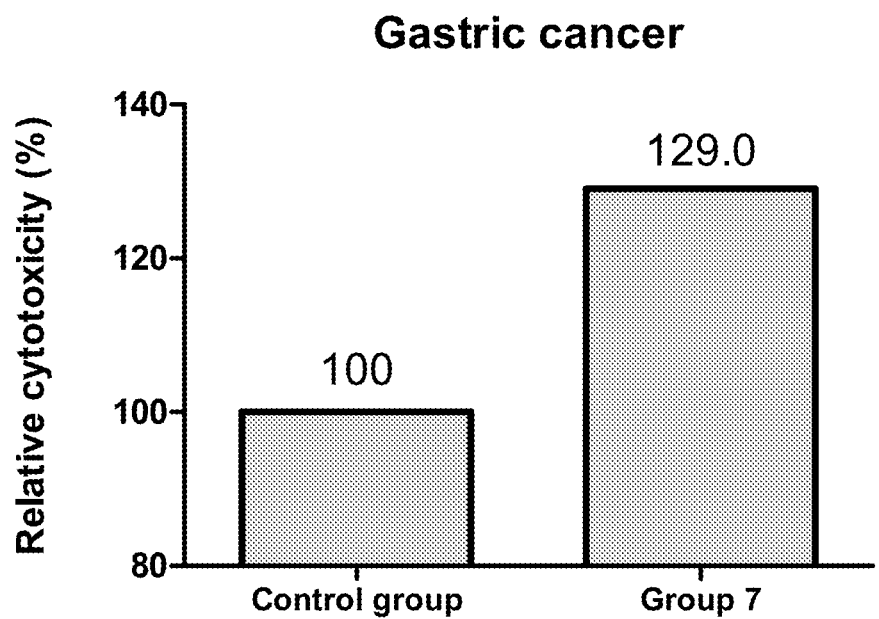

[Fig. 7a]
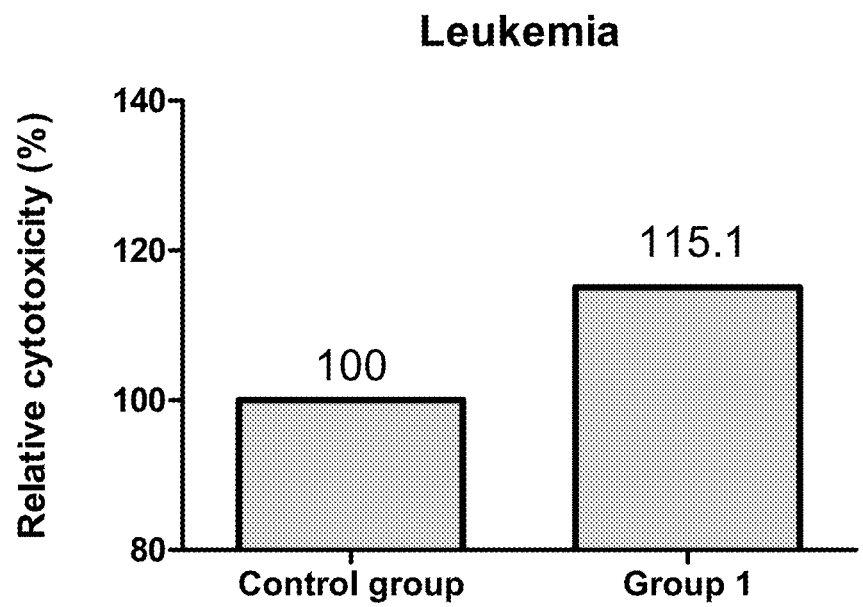
[Fig. 7b]
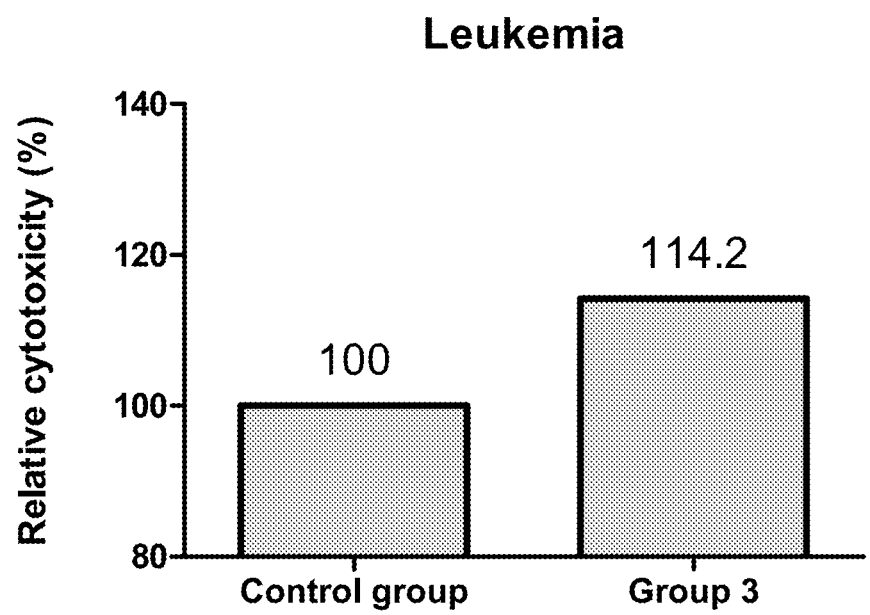

[Fig. 7c]
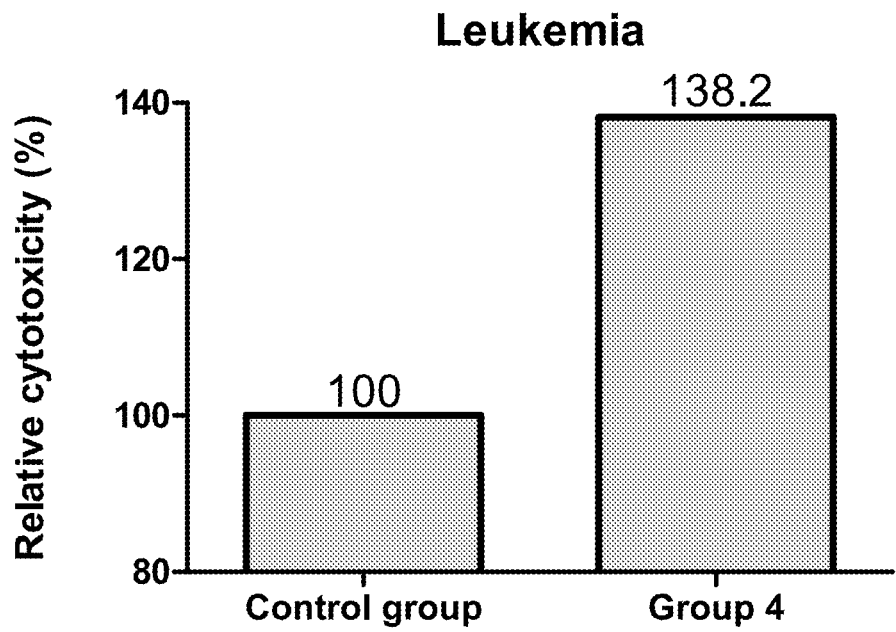
[Fig. 7d]
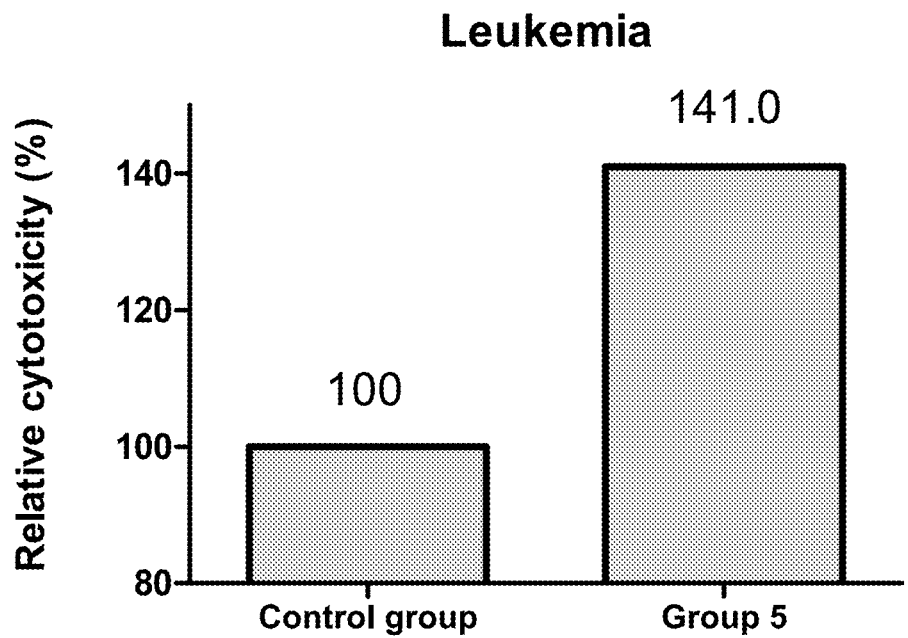

[Fig. 8a]
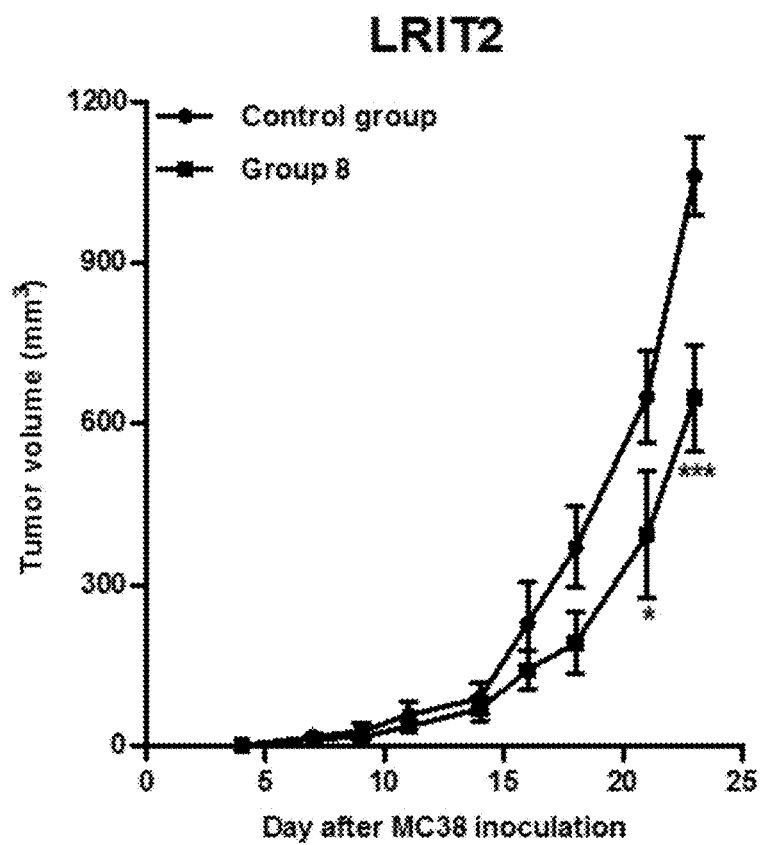

[Fig. 8b]
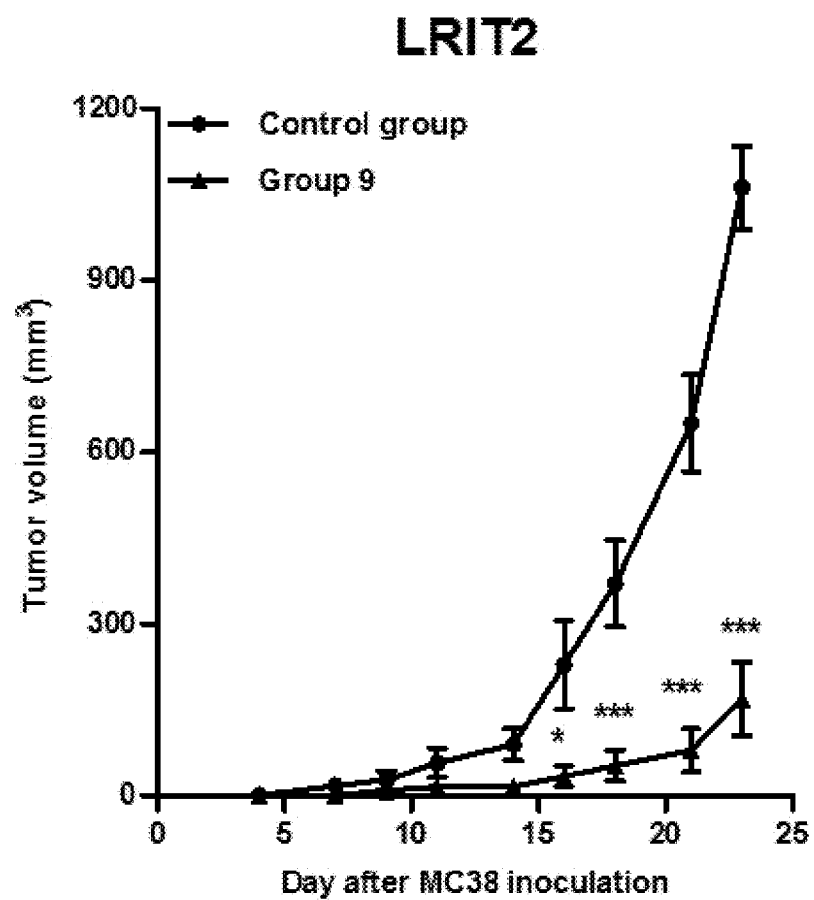

[Fig. 8c]
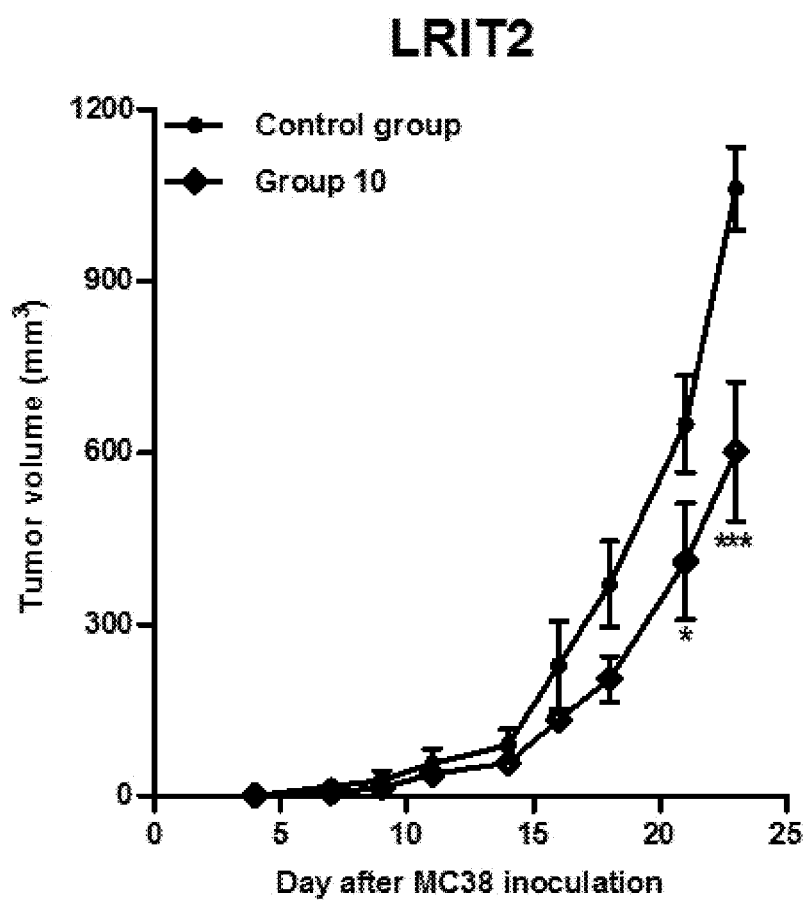

[Fig. 8d]
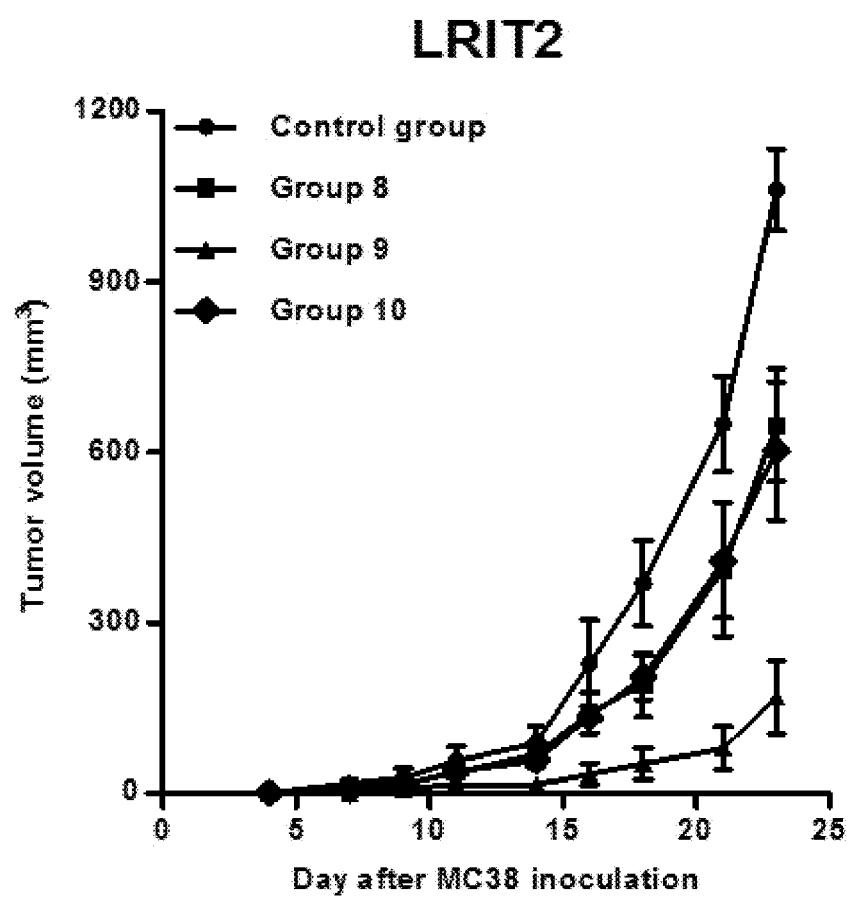

SEQUENCE LISTING

<160> NUMBER OF SEQ ID NOS: 14

<210> SEQ ID NO 1
<211> LENGTH: 550
<212> TYPE: PRT
<213> ORGANISM: Artificial Sequence
<220> FEATURE:
<223> OTHER INFORMATION: LRIT2

<400> SEQUENCE: 1

```
Met Ala Ser Val Phe His Tyr Phe Leu Leu Val Leu Val Phe Leu Asp
1               5                   10                  15

Thr His Ala Ala Gln Pro Phe Cys Leu Pro Gly Cys Thr Cys Ser Glu
            20                  25                  30

Glu Ser Phe Gly Arg Thr Leu Gln Cys Thr Ser Val Ser Leu Gly Lys
        35                  40                  45

Ile Pro Gly Asn Leu Ser Glu Glu Phe Lys Gln Val Arg Ile Glu Asn
    50                  55                  60

Ser Pro Leu Phe Glu Met Pro Gln Gly Ser Phe Ile Asn Met Ser Thr
65                  70                  75                  80

Leu Glu Tyr Leu Trp Leu Asn Phe Asn Asn Ile Ser Val Ile His Leu
                85                  90                  95

Gly Ala Leu Glu His Leu Pro Glu Leu Arg Glu Leu Arg Leu Glu Gly
            100                 105                 110

Asn Lys Leu Cys Ser Val Pro Trp Thr Ala Phe Arg Ala Thr Pro Leu
        115                 120                 125

Leu Arg Val Leu Asp Leu Lys Arg Asn Lys Ile Asp Ala Leu Pro Glu
    130                 135                 140

Leu Ala Leu Gln Phe Leu Val Ser Leu Thr Tyr Leu Asp Leu Ser Ser
145                 150                 155                 160

Asn Arg Leu Thr Val Val Ser Lys Ser Val Phe Leu Asn Trp Pro Ala
                165                 170                 175

Tyr Gln Lys Cys Arg Gln Pro Asp Cys Gly Ala Glu Ile Leu Ser Ser
            180                 185                 190

Leu Val Val Ala Leu His Asp Asn Pro Trp Val Cys Asp Cys Arg Leu
        195                 200                 205

Arg Gly Leu Val Gln Phe Val Lys Ser Ile Thr Leu Pro Val Ile Leu
    210                 215                 220

Val Asn Ser Tyr Leu Ile Cys Gln Gly Pro Leu Ser Lys Ala Gly Gln
225                 230                 235                 240

Leu Phe His Glu Thr Glu Leu Ser Ala Cys Met Lys Pro Gln Ile Ser
                245                 250                 255

Thr Pro Ser Ala Asn Ile Thr Ile Arg Ala Gly Gln Asn Val Thr Leu
            260                 265                 270

Arg Cys Leu Ala Gln Ala Ser Pro Ser Pro Ser Ile Ala Trp Thr Tyr
        275                 280                 285

Pro Leu Ser Met Trp Arg Glu Phe Asp Val Leu Thr Ser Ser Thr Gly
    290                 295                 300

Glu Asp Thr Ala Leu Ser Glu Leu Ala Ile Pro Ala Ala His Leu Val
305                 310                 315                 320

Asp Ser Gly Asn Tyr Thr Cys Met Ala Ser Asn Ser Ile Gly Lys Ser
                325                 330                 335

Asn Leu Val Ile Ser Leu His Val Gln Pro Ala Gln Ala Leu His Ala
            340                 345                 350

Pro Asp Ser Leu Ser Ile Pro Ser Glu Gly Asn Ala Tyr Ile Asp Leu
```

|     |     |     |     | 355 |     |     |     |     | 360 |     |     |     |     | 365 |
| --- | --- | --- | --- | --- | --- | --- | --- | --- | --- | --- | --- | --- | --- | --- |

Arg Val Val Lys Gln Thr Val His Gly Ile Leu Leu Glu Trp Leu Ala
    370                 375                 380

Val Ala Asp Thr Ser Lys Glu Glu Trp Phe Thr Leu Tyr Ile Ala Ser
385                 390                 395                 400

Asp Glu Ala Phe Arg Lys Glu Val Val His Ile Gly Pro Gly Ile Asn
                405                 410                 415

Thr Tyr Ala Val Asp Asp Leu Leu Pro Gly Thr Lys Tyr Glu Ala Cys
            420                 425                 430

Leu Ser Leu Glu Gly Gln Pro Pro His Gln Gly Gln Cys Val Ala Phe
            435                 440                 445

Val Thr Gly Arg Asp Ala Gly Gly Leu Glu Ala Arg Glu His Leu Leu
        450                 455                 460

His Val Thr Val Val Leu Cys Val Val Leu Leu Ala Val Pro Val Gly
465                 470                 475                 480

Ala Tyr Ala Trp Ala Ala Gln Gly Pro Cys Ser Cys Ser Lys Trp Val
                485                 490                 495

Leu Arg Gly Cys Leu His Arg Arg Lys Ala Pro Ser Cys Thr Pro Ala
            500                 505                 510

Ala Pro Gln Ser Lys Asp Gly Ser Phe Arg Glu His Pro Ala Val Cys
        515                 520                 525

Asp Asp Gly Glu Gly His Ile Asp Thr Glu Gly Asp Lys Glu Lys Gly
    530                 535                 540

Gly Thr Glu Asp Asn Ser
545                 550

<210> SEQ ID NO 2
<211> LENGTH: 1653
<212> TYPE: DNA
<213> ORGANISM: Artificial Sequence
<220> FEATURE:
<223> OTHER INFORMATION: LRIT2

<400> SEQUENCE: 2
atggcttcag ttttcatta cttcctgtta gttctggtct ttctggatac acacgcagct      60
cagcctttct gtctgccagg atgcacttgc tcagaggaga gttttggcag gactctgcag     120
tgcacatctg tctccttggg aaagatccct gggaaccttt ctgaagagtt caagcaagtg     180
agaattgaaa attcaccctt atttgagatg ccccaagggt cttccatcaa catgagcacc     240
ttggaatacc tctggctcaa ttttaacaat atcagtgtga tccacctagg agccctggaa     300
cacctgccag aactgaggga gctgagactg aggggaaca agctctgctc agtaccatgg     360
acagcgttcc gtgccacccc tctcctgagg gtcttggatc tcaaacgcaa caagattgat     420
gcactccctg agctggctct tcaattcttg gtcagcctga cctaccttga cctatcctcc     480
aataggctta cagttgtatc caagagtgtc ttcctgaact ggccagccta ccagaaatgc     540
cggcagcctg actgtgggc tgagattctc tccagcctgg tggtgccct gcatgacaac      600 ccctgggtat gtgactgtcg cctaaggggg cttgtccagt tgtcaagtc cattacccctc    660 ccagtcatcc tggtgaattc ctacctgata tgtcagggcc ctctgtccaa ggcagggcag    720 cttttttcatg aaactgagct agtgcttgc atgaagccac agatctcaac ccccagtgcc    780
aatatcacca tccgggcagg acagaatgtg accctgcgat gcttggcaca ggccagcccc    840
tcaccatcca ttgcatggac ttatcccctg agtatgtgga gagaatttga tgtgttgaca    900
tcttctactg gagaagacac tgctctgtca gagctggcca tacctgctgc ccacctggta    960

```
gacagtggta attacacctg catggcctcc aactccattg gcaagagcaa ccttgtaatc    1020
tctctccatg tccagcctgc ccaggcccta catgcacctg attctctttc catcccctcg    1080
gagggcaatg cctacattga cctgcgggtt gtcaagcaga cagtgcatgg gattttgctg    1140
gagtggcttg cagtgctga cacctctaag gaggagtggt tcaccctcta cattgcatcg     1200
gatgaagcct tcaggaagga ggtggttcac attggccccg gaatcaatac ttatgctgtg    1260
gatgacctcc ttcctggcac aaaatatgag gcctgcctca gcctagaggg ccagcctcca    1320
caccagggcc agtgtgtagc ttttgtaaca ggcagagatg ctggtgggct agaggcacgt    1380
gagcacctcc tgcatgtcac agtggtcctg tgtgtggtgc tgcttgcagt gcctgtgggc    1440
gcctatgcct gggcagccca gggcccctgc agctgcagca agtgggtcct gcgcggctgt    1500
cttcatcgca ggaaagcccc cagctgcacc cctgcagccc cgcagtccaa ggatggctcc    1560
tttagagaac atccagctgt ctgtgatgac ggtgaagggc acatagacac tgaggggggac   1620 aaggagaaag gaggaacgga agacaacagc tga                                 1653
```

<210> SEQ ID NO 3
<211> LENGTH: 19
<212> TYPE: RNA
<213> ORGANISM: Artificial Sequence
<220> FEATURE:
<223> OTHER INFORMATION: human LRIT2 siRNA-sense(Group 5)

<400> SEQUENCE: 3
gagcuuagug cuugcauga                                                 19

<210> SEQ ID NO 4
<211> LENGTH: 19
<212> TYPE: RNA
<213> ORGANISM: Artificial Sequence
<220> FEATURE:
<223> OTHER INFORMATION: human LRIT2 siRNA-antisense(Group 5)

<400> SEQUENCE: 4
ucaugcaagc acuaagcuc                                                 19

<210> SEQ ID NO 5
<211> LENGTH: 19
<212> TYPE: RNA
<213> ORGANISM: Artificial Sequence
<220> FEATURE:
<223> OTHER INFORMATION: human LRIT2 siRNA-sense(Group 6)

<400> SEQUENCE: 5
cuacauugca ucggaugaa                                                 19

<210> SEQ ID NO 6
<211> LENGTH: 19
<212> TYPE: RNA
<213> ORGANISM: Artificial Sequence
<220> FEATURE:
<223> OTHER INFORMATION: human LRIT2 siRNA-antisense(Group 6)

<400> SEQUENCE: 6
uucauccgau gcaauguag                                                 19

<210> SEQ ID NO 7
<211> LENGTH: 19
<212> TYPE: RNA
<213> ORGANISM: Artificial Sequence
<220> FEATURE:

```
<223> OTHER INFORMATION: human LRIT2 siRNA-sense(Group 7)

<400> SEQUENCE: 7
uguguugaca ucuucuacu                                                    19

<210> SEQ ID NO 8
<211> LENGTH: 19
<212> TYPE: RNA
<213> ORGANISM: Artificial Sequence
<220> FEATURE:
<223> OTHER INFORMATION: human LRIT2 siRNA-antisense(Group 7)

<400> SEQUENCE: 8
aguagaagau gucaacaca                                                    19

<210> SEQ ID NO 9
<211> LENGTH: 19
<212> TYPE: RNA
<213> ORGANISM: Artificial Sequence
<220> FEATURE:
<223> OTHER INFORMATION: mouse LRIT2 siRNA-sense(Group 8)

<400> SEQUENCE: 9
cucuucaguu ccuaaccaa                                                    19

<210> SEQ ID NO 10
<211> LENGTH: 19
<212> TYPE: RNA
<213> ORGANISM: Artificial Sequence
<220> FEATURE:
<223> OTHER INFORMATION: mouse LRIT2 siRNA-antisense(Group 8)

<400> SEQUENCE: 10
uugguuagga acugaagag                                                    19

<210> SEQ ID NO 11
<211> LENGTH: 19
<212> TYPE: RNA
<213> ORGANISM: Artificial Sequence
<220> FEATURE:
<223> OTHER INFORMATION: mouse LRIT2 siRNA-sense(Group 9)

<400> SEQUENCE: 11
gucacuaucc agguaggaa                                                    19

<210> SEQ ID NO 12
<211> LENGTH: 19
<212> TYPE: RNA
<213> ORGANISM: Artificial Sequence
<220> FEATURE:
<223> OTHER INFORMATION: mouse LRIT2 siRNA-antisense(Group 9)

<400> SEQUENCE: 12
uuccuaccug gauagugac                                                    19

<210> SEQ ID NO 13
<211> LENGTH: 19
<212> TYPE: RNA
<213> ORGANISM: Artificial Sequence
<220> FEATURE:
<223> OTHER INFORMATION: mouse LRIT2 siRNA-sense(Group 10)

<400> SEQUENCE: 13
cagacaacuu ucccgaaga                                                    19
```

```
<210> SEQ ID NO 14
<211> LENGTH: 19
<212> TYPE: RNA
<213> ORGANISM: Artificial Sequence
<220> FEATURE:
<223> OTHER INFORMATION: mouse LRIT2 siRNA-antisense(Group 10)

<400> SEQUENCE: 14
ucuucgggaa aguugucug                                                   19
```

PHARMACEUTICAL COMPOSITION FOR PREVENTING OR TREATING CANCER COMPRISING LRIT2 INHIBITOR AS ACTIVE INGREDIENT

CROSS REFERENCE TO RELATED APPLICATIONS

This application is a National Stage of International Application No. PCT/KR2019/005853 filed May 15, 2019, claiming priority based on Korean Patent Application No. 10-2018-0055909 filed May 16, 2018, the entire disclosures of which are incorporated herein by reference.

TECHNICAL FIELD

The present invention relates to a pharmaceutical composition for preventing or treating cancer, comprising an LRIT2 inhibitor as an active ingredient.

BACKGROUND ART

T cells are cells that play an important role in immunity of the human body. T cells are divided into killer T cells, helper T cells, regulatory T cells, and memory T cells. In particular, killer T cells express CD8 on the cell surface; helper T cells express CD4 on the cell surface; and regulatory T cells express CD4 and CD25 on the cell surface.

When an antigen such as a bacterium enters from the outside, helper T cells secrete substances such as cytokines to activate killer T cells and B cells. The activated killer T cells kill pathogen-infected cells, and the activated B cells secrete antibodies to inhibit activity of the antigen. Recently, attempts have been made to treat diseases such as cancer by activating such an immunoregulatory ability of T cells.

In addition, a T cell-mediated disease is recognized as a disease representing various immune-system diseases. In particular, T cells are considered as causing and perpetuating autoimmune diseases. Immune responses to self-antigens are caused by continuous or periodic activation of autoreactive T cells. In addition, the autoreactive T cells are attracting attention as a cause for characteristic tissue injury and tissue destruction which are directly or indirectly identified in autoimmune diseases.

Meanwhile, programmed cell death ligand 1 (PD-L1) is a type 1 transmembrane protein which is a ligand for programmed cell death-1 (PD-1). PD-L1 is expressed in hematopoietic cells such as T lymphocytes, B lymphocytes, dendritic cells, or macrophages. PD-1 is known as an immune checkpoint factor or immunomodulator which regulates secondary signaling activity of T cells. In addition, it has been reported that PD-1 is capable of acting to inhibit functions of T cells, such as inhibiting proliferation of T cells and decreasing expression of cytokines, through binding to PD-L1 or the like which is expressed on the surface of cells such as activated T cells or dendritic cells (Krzysztof M. Zak, et al., 2015).

Recently, attempts have been made to develop anticancer agents and immunomodulators using substances that regulate immune functions of T cells, such as PD-1 and PD-L1.

DISCLOSURE OF INVENTION

Technical Problem

Accordingly, in the course of researching substances capable of inhibiting or increasing activity of immune cells, the present inventors have identified that the LRIT2 cell signaling system can regulate activity of T cells, and thus have completed the present invention.

Solution to Problem

In an embodiment, there is provided an immunopotentiator comprising, as an active ingredient, a substance that binds to LRIT2 protein or a substance that inhibits expression of LRIT2 gene.

In addition, in an embodiment, there is provided a pharmaceutical composition for preventing or treating cancer, comprising, as an active ingredient, a substance that binds to LRIT2 protein or a substance that inhibits expression of LRIT2 gene.

In addition, in an embodiment, there is provided a method for treating cancer, comprising a step of administering the pharmaceutical composition to an individual.

Advantageous Effects of Invention

The LRIT2 inhibitor according to the present invention can increase activity of immune cells, and thus can be used as an immunopotentiator. In addition, the LRIT2 inhibitor according to the present invention can potentiate immunity of an individual, and thus can be used to effectively prevent or treat cancer.

BRIEF DESCRIPTION OF DRAWINGS

FIG. 1 illustrates that LRIT2 inhibits maturation of T cells into CD4+ T cells.

FIG. 2 illustrates that LRIT2 inhibits maturation of T cells into CD8+ T cells.

FIGS. 3a to 3d illustrate cytotoxicity (%) of peripheral blood mononuclear cells (PBMCs) per group, obtained in a case where the lung cancer cell line A549 and PBMCs are treated with an LRIT2 inhibitor (antibody or siRNA).

FIGS. 4a to 4d illustrate cytotoxicity (%) of PBMCs per group, obtained in a case where the colon cancer cell line HCT-116 and PBMCs are treated with an LRIT2 inhibitor (antibody or siRNA).

FIGS. 5a to 5d illustrate cytotoxicity (%) of PBMCs per group, obtained in a case where the breast cancer cell line MDA-MB-231 and PBMCs are treated with an LRIT2 inhibitor (antibody or siRNA).

FIGS. 6a to 6d illustrate cytotoxicity (%) of PBMCs per group, obtained in a case where the gastric cancer cell line MKN-74 and PBMCs are treated with an LRIT2 inhibitor (antibody or siRNA).

FIGS. 7a to 7d illustrate cytotoxicity (%) of PBMCs per group, obtained in a case where the blood cancer cell line U937 and PBMCs are treated with an LRIT2 inhibitor (antibody or siRNA).

FIGS. 8a to 8d illustrate changes in tumor size in mice treated with an LRIT2 inhibitor (each of 3 types of siRNAs), per group.

BEST MODE FOR CARRYING OUT THE INVENTION

In an embodiment, there is provided an immunopotentiator comprising, as an active ingredient, a substance that binds to leucine-rich repeat, immunoglobulin-like domain and transmembrane domain-containing protein 2 (LRIT2) protein or a substance that inhibits expression of LRIT2 gene.

As used herein, the term "LRIT2" is the abbreviation of "leucine-rich repeat, immunoglobulin-like domain and transmembrane domain-containing protein 2", and may be a protein having the amino acid sequence of SEQ ID NO: 1. The protein having the amino acid sequence of SEQ ID NO: 1 may be encoded by a polynucleotide having the nucleotide sequence of SEQ ID NO: 2.

In the present invention, the substance that binds to LRIT2 protein may be a compound, an aptamer, a peptide, or an antibody or a fragment thereof which specifically binds to the LRIT2 protein. The antibody or a fragment thereof may be any one selected from the group consisting of a monoclonal antibody, scFv, Fab, Fab', and F(ab)'.

In the present invention, the substance that inhibits expression of LRIT2 gene may be an antisense nucleic acid, siRNA, shRNA, miRNA, or ribozyme which complementarily binds to DNA or mRNA of the LRIT2 gene. The LRIT2 siRNA may be any one of the nucleotide sequences of SEQ ID NOS: 3 to 14.

In one embodiment of the present invention, it was intended to identify whether an anti-LRIT2 antibody or LRIT2 siRNA, which targets LRIT2 and inhibits activity thereof, can increase cytotoxicity of peripheral blood mononuclear cells (PBMCs) against cancer cells. As a result, in a mixture of PBMCs and a cancer cell line which had been treated with an LRIT2 inhibitor, cytotoxicity of the PBMCs against the cancer cell line was exhibited at a higher level than a control group. In addition, in another embodiment of the present invention, it was intended to identify whether LRIT2 siRNA that inhibits activity of LRIT2 inhibits growth of tumors in mice. As a result, in mice in which LRIT2 had been knocked down by treatment with LRIT2 siRNA, a remarkably inhibited tumor growth rate was exhibited as compared with a control group. As can be seen from the above results, the anti-LRIT2 antibody or LRIT2 siRNA, which targets LRIT2 and inhibits activity thereof, blocks or knocks down LRIT2 and inhibits activity or expression thereof, so that progress of cancer is delayed or stopped.

In addition, in an embodiment, there is provided a pharmaceutical composition for preventing or treating cancer, comprising, as an active ingredient, a substance that binds to LRIT2 protein or a substance that inhibits expression of LRIT2 gene.

The substance that binds to LRIT2 protein or the substance that inhibits expression of LRIT2 gene is as described above. The pharmaceutical composition may further comprise a pharmaceutically acceptable additive.

In the present invention, the cancer may be, but is not limited to, any one selected from the group consisting of bladder cancer, bone cancer, blood cancer, breast cancer, melanoma, thyroid cancer, parathyroid cancer, bone marrow cancer, rectal cancer, throat cancer, laryngeal cancer, lung cancer, esophageal cancer, pancreatic cancer, colorectal cancer, gastric cancer, tongue cancer, skin cancer, brain tumor, uterine cancer, head or neck cancer, gallbladder cancer, oral cancer, colon cancer, perianal cancer, central nervous system tumor, and liver cancer.

A preferred daily dose of the pharmaceutical composition for preventing or treating cancer, comprising, as an active ingredient, a substance that binds to LRIT2 protein or a substance that inhibits expression of LRIT2 gene according to the present invention may be in a range of 0.01 ug/kg to 10 g/kg and preferably 0.01 mg/kg to 1 g/kg, depending on the patient's condition, body weight, sex, age, severity of disease, and route of administration. Administration may be carried out once or several times a day.

In addition, in an embodiment, there is provided a method for treating cancer, comprising a step of administering, to an individual, a pharmaceutical composition for preventing or treating cancer, comprising, as an active ingredient, a substance that binds to LRIT2 protein or a substance that inhibits expression of LRIT2 gene.

The route of administration may be, but is not limited to, any one selected from the group consisting of intravenous, intramuscular, intradermal, subcutaneous, intraperitoneal, intraarteriole, intraventricular, intralesional, intrathecal, topical, and combinations thereof.

MODE FOR THE INVENTION

Hereinafter, the present invention will be described in more detail by way of the following examples. However, the following examples are intended to only illustrate the present invention, and the scope of the present invention is not limited thereto.

Preparation Example 1. Preparation of Buffers

Buffers used in the examples were prepared as follows:
1×PBS (Thermo Fisher gibco #10010) was prepared by mixing 155 mM sodium chloride, 2.96 mM sodium phosphate solution, and 1.05 mM potassium phosphate solution, pH 7.4.

FACS buffer was prepared by mixing 1×PBS (Thermo Fisher gibco #10010), 10 ml of 2% FBS (Thermo Fisher gibco #16000-044), and 1 ml of 1 mM EDTA (Fisher 15575020).

1×RBC lysis buffer was prepared by diluting 10×RBC solution (Biolegend #420301) in triple-distilled water at 1:10.

10% FBS RPMI1640 was prepared by mixing RPMI medium (Cellgrow #10-040-CVR), 50 ml of 10% FBS (Thermo Fisher gibco #16000-044), 5 ml of 1% antibiotics (Thermo Fisher gibco #15140-122), and 0.5 ml of 2-mercaptoethanol (Thermo Fisher gibco #21985-023).

MACS buffer was prepared by mixing 1×PBS (Thermo Fisher gibco #10010), 0.5% bovine serum albumin (BSA) (Millipore #82-100-6), and 2 ml of 2 mM EDTA (Fisher 15575020).

Example 1. Identification of Inhibitory Effect of LRIT2 Protein on Proliferation and Activity of T Cells In the present example, it was intended to identify whether LRIT2 protein inhibits proliferation and activity of T cells, and thus causes cancer cells to avoid the T cell-mediated immune system.

Example 1.1. Preparation of CD4+ T Cells and CD8+ T Cells

Human blood was collected and placed in a 10-mL tube coated with EDTA (or heparin). The human blood was mixed with PBS at a ratio of 1:1. Then, Ficoll-Paque PLUS was placed in a 50-mL tube, and the above blood sample was added thereto. After centrifugation, human PBMCs were collected. The collected product was centrifuged to remove the supernatant. Subsequently, RBC lysis (1×) buffer was added thereto, pipetting was performed, and then the resultant was kept on ice for 3 minutes. Subsequently, 50 ml of 10% FBS RPMI1640 was added thereto and the mixture was centrifuged to remove supernatant. Then, FACS buffer was added thereto and centrifugation was performed to remove the supernatant. Thereafter, 50 ml of MACS buffer (PBS containing 0.5% BSA and 2 mM EDTA) was added thereto, the number of cells was counted, and centrifugation was performed to remove the supernatant.

CD4+ T cells and CD8+ T cells were resuspended using 40 µl of MACS buffer per $1 \times 10^7$ cells. 10 µl of each of anti-CD4 and anti-CD8 biotin antibodies was placed in the tube, and then the tube was kept in a refrigerator for 5 minutes. Thereafter, 30 µl of MACS buffer per $1 \times 10^7$ cells was added to the resulting product. 20 µl of anti-biotin microbeads was added thereto and mixing was performed. Subsequently, CD4+ T cells and CD8+ T cells were isolated using LS column and the number of the respective cells was counted.

Each of the prepared CD4+ T cells and CD8+ T cells was mixed with 1 µl of carboxyfluorescein succinimidyl ester (CFSE) per $2 \times 10^6$ cells and each mixture was kept at 37° C. for 3 minutes. Then, FBS was added to each tube containing each of CD4+ T cells and CD8+ T cells, and each tube was kept on ice for 10 minutes. Thereafter, centrifugation was performed to remove the supernatant. 30 ml of FACS buffer was added to the resulting product, and then pipetting was performed. Centrifugation was performed to remove the supernatant. Then, 10% FBS RPMI1640 was added thereto, and then pipetting was performed. Centrifugation was performed to remove the supernatant. Thereafter, the resulting product was mixed with 10 ml of 10% FBS RPMI1640, and then the number of cells was counted.

Example 1.2. Identification of Inhibited Activity of T Cells Caused by LRIT2 Protein Recombinant human IgG1 protein (Cat. No. 110-HG) and recombinant human PD-L1/B7-H1 protein (Cat. No. 156-B7) were purchased from R&D Systems. In addition, recombinant human LRIT2 protein (Cat. No. 8388-LR-050) was purchased from Sino Biological Inc.

10 µg/ml of each of the proteins was mixed, respectively, with 2 µg/ml, 3 µg/ml, 4 µg/ml, and 6 µg/ml of anti-CD3 antibody (BioLegend, Cat. No. 317325). Each of the mixtures was used to coat a 96-well plate at 4° C., and washing was performed three times with PBS. Each of the CD4+ T cells and the CD8+ T cells prepared in Example 1.1 was added at 200 µl in an amount of $2 \times 10^6$ cells per each well of the 96-well plate and incubation was performed. Activation of the CD4+ T cells and the CD8+ T cells using the anti-CD3 antibody was allowed to occur for 72 hours. Here, proliferation of the CD4+ T cells and the CD8+ T cells was identifiable by a level of CFSE staining, and was analyzed by flow cytometry using FACSDiVa software (BD Biosciences). The results are illustrated in FIGS. 1 and 2.

FIGS. 1 and 2 are bar graphs, respectively representing proliferation rates (%) of the CD4+ T cells and the CD8+ T cells measured by flow cytometry. As illustrated in FIGS. 1 and 2, in the control group treated with PD-L1, proliferation of both the CD4+ T cells and the CD8+ T cells was inhibited as compared with the control group treated with IgG1.

In addition, in the group treated with LRIT2, proliferation of the CD4+ T cells and the CD8+ T cells was remarkably inhibited as compared with the control group treated with IgG1, and proliferation of the CD4+ T cells and the CD8+ T cells was inhibited at a similar level to the control group treated with PD-L1. From these results, it can be seen that neutralization of LRIT2 due to its blocking or knockdown decreases an inhibitory ability of LRIT2 on proliferation of T cells, and thus enables effective treatment of cancer.

Example 2. PBMC Cytotoxicity Assay

In the present example, it was intended to identify whether in a case where LRIT2 is neutralized using an LRIT2 inhibitor, PBMCs are capable of increasing cytotoxicity (killing ability) against cancer cells.

Example 2.1. Preparation of PBMCs

Human blood was collected and placed in a 10-mL tube coated with EDTA (or heparin). The human blood was mixed with PBS at a ratio of 1:1. Then, Ficoll-Paque PLUS was placed in a 50-mL tube, and the above blood sample was added thereto. After centrifugation, human PBMCs were collected.

1.0 µg/ml of anti-CD3 antibody (BioLegend, Cat. No. 317325) was used to coat a 96-well plate at 4° C. Each well of the 96-well plate was washed 3 times with PBS before addition of the PBMCs. The previously obtained PBMCs were mixed with 10% FBS RPMI1640 and added at 100 µl in an amount of $6 \times 10^5$ cells per each well of the 96-well plate. Activation of the PBMCs by the anti-CD3 antibody was allowed to occur for 72 hours.

Example 2.2. Preparation of Cancer Cells

Lung cancer cell line A549 (ATCC®CCL-185), colon cancer cell line HCT-116 (ATCC®CCL-247), breast cancer cell line MDA-MB-231 (ATCC®HTB-26), gastric cancer cell line MKN-74 (KCLB No. 80104), and leukemia cell line U937 (ATCC®CRL-1593.2) were each mixed with 5 µM of CFSE and kept at 37° C. for 5 minutes. Thereafter, FBS was added to each tube containing each cell line, and each tube was kept on ice for 10 minutes. Subsequently, centrifugation was performed to remove the supernatant. To the product thus obtained was added 30 ml of FACS buffer. Then, pipetting was performed and centrifugation was performed to remove the supernatant. Then, 10% FBS RPMI1640 was added thereto. Then, pipetting was performed and centrifugation was performed to remove the supernatant. The product thus obtained was mixed with 10 ml of 10% FBS RPMI1640, and then the number of cells was counted.

Each type of the cancer cells was added at $3 \times 10^4$ cells/100 µl per each PBMC-containing well of the 96-well plate prepared in Example 2.1, and incubation was performed.

Example 2.3. Measurement of Cytotoxicity of PBMCs Against Cancer Cell Lines

10 µg/mL of anti-human LRIT2 antibody or 50 nM LRIT2 siRNA was added to each well of the 96-well plate, and incubation was performed for 24 hours. Table 1 below shows experimental groups, in which four types of neutralizing antibodies are used to block LRIT2, and an untreated control group; and Table 2 below shows experimental groups, in which three types of siRNAs are used to knock down LRIT2, and an untreated control group.

TABLE 1

| | Human LRIT2 neutralizing antibody |
|---|---|
| Control group | Untreated |
| Group 1 | anti-human LRIT2 antibody (Biorbyt Ltd., orb185006) |
| Group 2 | anti-human LRIT2 antibody (Thermo Fisher Scientific, PA5-58105) |
| Group 3 | anti-human LRIT2 antibody (Atlas Antibodies, HPA037788) |
| Group 4 | anti-human LRIT2 antibody (Novus Biologicals, NBP1-90876) |

TABLE 2

| | Human LRIT2 siRNA |
|---|---|
| Control group | Untreated |
| Group 5 | Sense (5'-GA GCU UAG UGC UUG CAU GA-3') (SEQ ID NO: 3)<br>Antisense (5'-UC AUG CAA GCA CUA AGC UC-3') (SEQ ID NO: 4) |
| Group 6 | Sense (5'-CU ACA UUG CAU CGG AUG AA-3') (SEQ ID NO: 5)<br>Antisense (5'-UU CAU CCG AUG CAA UGU AG-3') (SEQ ID NO: 6) |
| Group 7 | Sense (5'-UG UGU UGA CAU CUU CUA CU-3') (SEQ ID NO: 7)<br>Antisense (5'-AG UAG AAG AUG UCA ACA CA-3') (SEQ ID NO: 8) |

Each mixture of PBMCs and each cancer cell line was incubated with the antibody or siRNA. After 24 hours, in order to identify lysed cells, the cells were stained with 7-aminoactinomycin D (7-AAD; BD Pharmingen, San Diego, Calif., USA). Staining for CFSE and 7-AAD was measured using the FACSDiVa software (BD Biosciences), to identify the PBMC's cytolytic ability against each cancer cell line. The results are illustrated in FIGS. 3a to 7d.

Specifically, the experimental results obtained in a case where the lung cancer cell line A549 is treated with the LRIT2 neutralizing antibody or siRNA are illustrated in FIGS. 3a to 3d. The experimental results obtained in a case where the colon cancer cell line HCT-116 is treated with the LRIT2 neutralizing antibody or siRNA are illustrated in FIGS. 4a to 4d. The experimental results obtained in a case where the breast cancer cell line MDA-MB-231 is treated with the LRIT2 neutralizing antibody or siRNA are illustrated in FIGS. 5a to 5d. The experimental results obtained in a case where the gastric cancer cell line MKN-74 is treated with the LRIT2 neutralizing antibody or siRNA are illustrated in FIGS. 6a to 6d. The experimental results obtained in a case where the leukemia cell line U937 is treated with the LRIT2 neutralizing antibody or siRNA are illustrated in FIGS. 7a to 7d.

As illustrated in FIGS. 3a to 3d, in a case where the lung cancer cell line A549 and PBMCs are treated with the LRIT2 neutralizing antibody, a significantly increased lung cancer cell-killing ability was exhibited as compared with the untreated control group, although there was a difference in degree, in terms of the killing ability, depending on types of antibodies; and even in a case where the lung cancer cell line is treated with LRIT2 siRNA, a significantly increased lung cancer cell-killing ability was also exhibited.

Similar to the above results that PBMCs exhibit an increased killing ability against the lung cancer cell line, it was identified that PBMCs also exhibit an increased killing ability against the colon cancer cell line, the breast cancer cell line, the gastric cancer cell line, and the leukemia cell line in a case where LRIT2 is neutralized using the LRIT2 neutralizing antibody or siRNA (FIGS. 4a to 7d).

Example 3. Experiments Using Tumor Mouse Model

In the present example, it was intended to identify in vivo whether growth of tumors in mice is inhibited in a case where LRIT2 is neutralized using an LRIT2 inhibitor.

The MC38 cell line derived from C57BL/6 colon adenocarcinoma cells was resuspended at a concentration of $2.0 \times 10^5$ cells in 50 µl of PBS and subcutaneously injected into the flank of 6-week-old female C57BL/6 mice. Table 3 below shows experimental groups, in which siRNA is used to knock down LRIT2, and an untreated control group.

TABLE 3

| | Mouse LRIT2 siRNA |
|---|---|
| Control group | Untreated |
| Group 8 | Sense (5'-CU CUU CAG UUC CUA ACC AA-3') (SEQ ID NO: 9)<br>Antisense (5'-UU GGU UAG GAA CUG AAG AG-3') (SEQ ID NO: 10) |
| Group 9 | Sense (5'-GU CAC UAU CCA GGU AGG AA-3') (SEQ ID NO: 11)<br>Antisense (5'-UU CCU ACC UGG AUA GUG AC-3') (SEQ ID NO: 12) |
| Group 10 | Sense (5'-CA GAC AAC UUU CCC GAA GA-3') (SEQ ID NO: 13)<br>Antisense (5'-UC UUC GGG AAA GUU GUC UG-3') (SEQ ID NO: 14) |

For all experimental groups, starting from the 11th day after injection of the MC38 cell line, each siRNA targeting mouse LRIT2 was injected into the mouse tumor three times in total at intervals of 5 days. Specifically, 10 µg of siRNA was mixed with 7.5 µl of Oligofectamine (Invitrogen) in PBS according to the manufacturer's instructions, and then the mixture was injected, at a dose of 0.5 mg/kg, directly into the tumor tissue induced in mice. The results obtained by measuring tumor size in mice in the untreated control group and the experimental groups, in which LRIT2 is knocked down, are illustrated in FIGS. 8a to 8d.

As illustrated in FIGS. 8a to 8d, it was found that in the untreated control group, the tumor has continuously grown since its generation in mice. On the other hand, it was found that in mice in which LRIT2 is knocked down, the tumor exhibits a remarkably inhibited growth rate as compared with the untreated control group. This shows that in a case where LRIT2 is blocked or knocked down and activity or expression thereof is inhibited, progress of cancer is delayed or stopped, and development of cancer is inhibited. Accordingly, an LRIT2 inhibitor can be usefully used to prevent and treat cancer.

The invention claimed is:

1. A method for treating cancer in a subject, comprising: administering, to the subject, a pharmaceutical composition,
wherein the pharmaceutical composition comprises a substance that binds to LRIT2 protein as an active ingredient,
wherein the substance that binds to LRIT2 protein is a neutralizing antibody or a fragment thereof which specifically binds to the LRIT2 protein.

2. The method of claim 1, wherein the cancer is any one selected from the group consisting of bladder cancer, bone cancer, blood cancer, breast cancer, melanoma, thyroid cancer, parathyroid cancer, bone marrow cancer, rectal cancer, throat cancer, laryngeal cancer, lung cancer, esophageal cancer, pancreatic cancer, colorectal cancer, gastric cancer, tongue cancer, skin cancer, brain tumor, uterine cancer, head or neck cancer, gallbladder cancer, oral cancer, colon cancer, perianal cancer, central nervous system tumor, and liver cancer.

3. The method of claim 1, wherein the LRIT2 protein has the amino acid sequence of SEQ ID NO: 1.

4. The method of claim 1, wherein the neutralizing antibody or the fragment thereof is any one selected from the group consisting of a monoclonal antibody, scFv, Fab, Fab', and F(ab)'.

5. The method of claim 1, wherein the DNA of the LRIT2 gene has the nucleotide sequence of SEQ ID NO: 2.

6. A method for enhancing cancer treatment of a subject comprising administering to the subject a pharmaceutical composition,
wherein the pharmaceutical composition comprises a substance that binds to LRIT2 protein as an active ingredient,
wherein the enhancing cancer treatment comprises an increase in number of T cells,
wherein the substance that binds to LRIT2 protein is a neutralizing antibody or a fragment thereof which specifically binds to the LRIT2 protein.

7. The method of claim 6, wherein the T cells are CD4+ T cells and CD8+ T cells.

8. The method of claim 6, wherein the LRIT2 protein has the amino acid sequence of SEQ ID NO: 1.

9. The method of claim 6, wherein the neutralizing antibody or the fragment thereof is any one selected from the group consisting of a monoclonal antibody, scFv, Fab, Fab', and F(ab)'.

10. The method of claim 6, wherein the DNA of the LRIT2 gene has the nucleotide sequence of SEQ ID NO: 2.

* * * * *